(12) United States Patent  
Domroese

(10) Patent No.: US 6,722,865 B2
(45) Date of Patent: Apr. 20, 2004

(54) UNIVERSAL TUBE CLAMP ASSEMBLY

(75) Inventor: Michael K. Domroese, Woodbury, MN (US)

(73) Assignee: Terumorcardiovascular Systems Corporation, Ann Arbor, MI (US)

( * ) Notice: Subject to any disclaimer, the term of this patent is extended or adjusted under 35 U.S.C. 154(b) by 285 days.

(21) Appl. No.: 09/947,753

(22) Filed: Sep. 7, 2001

(65) Prior Publication Data

US 2003/0049144 A1 Mar. 13, 2003

(51) Int. Cl.⁷ ................................. F04B 43/08
(52) U.S. Cl. ................................. 417/477.11
(58) Field of Search .............. 417/477.11, 477.3, 417/477.8, 477.13

(56) References Cited

U.S. PATENT DOCUMENTS

| 3,411,534 A | 11/1968 | Rose |
|---|---|---|
| 4,006,874 A | 2/1977 | McGee |
| 4,021,178 A | 5/1977 | Braun |
| 4,373,525 A | 2/1983 | Kobayashi |
| 4,483,334 A | 11/1984 | Murray |
| 4,552,516 A | 11/1985 | Stanley |
| 4,558,996 A | 12/1985 | Becker |
| 4,586,883 A | 5/1986 | Sumner |
| 4,596,547 A | 6/1986 | Troutner |
| 4,597,690 A | 7/1986 | Girard |
| 4,640,536 A | 2/1987 | Printiss, Sr. et al. |
| 4,767,289 A | 8/1988 | Parrott et al. |
| 4,861,242 A | 8/1989 | Finsterwald |
| 4,863,203 A | 9/1989 | Mitchell, Jr. |
| 4,925,376 A | 5/1990 | Kahler |
| 4,950,136 A | 8/1990 | Haas et al. |
| 4,953,899 A | 9/1990 | Printiss, Sr. |
| 4,976,593 A | 12/1990 | Miyamoto |
| 5,017,192 A | 5/1991 | Dodge et al. |
| 5,098,047 A | 3/1992 | Plumley |
| 5,110,270 A | 5/1992 | Morrick |
| 5,276,949 A | 1/1994 | Cordellini |
| 5,290,239 A | 3/1994 | Classey et al. |

(List continued on next page.)

FOREIGN PATENT DOCUMENTS

| FR | 2 680 714 | 3/1993 |
|---|---|---|
| GB | 2 130 933 | 6/1984 |
| GB | 2 311 664 | 10/1997 |
| NL | 7 308 538 | 12/1974 |

Primary Examiner—Edward K. Look
Assistant Examiner—Vinod D. Patel
(74) Attorney, Agent, or Firm—Burns, Doane, Swecker & Mathis, L.L.P.

(57) ABSTRACT

A clamp assembly for flexible tubing including a housing, at least one movable slide disposed within the housing, an opening defined between each side of the at least one slide and the housing for receiving flexible tubing, and a control element, rotation of the control element displacing the at least one slide in a predetermined direction to facilitate insertion of flexible tubing in the respective opening.

20 Claims, 10 Drawing Sheets

U.S. PATENT DOCUMENTS

| | | | |
|---|---|---|---|
| 5,300,044 A | 4/1994 | Classey et al. | |
| 5,332,184 A | 7/1994 | Davis | |
| 5,413,566 A | 5/1995 | Sevrain et al. | |
| 5,433,588 A | 7/1995 | Monk et al. | |
| 5,447,417 A | 9/1995 | Kuhl et al. | |
| 5,453,098 A | 9/1995 | Botts et al. | |
| 5,544,396 A | 8/1996 | Mekyska | |
| 5,548,873 A * | 8/1996 | Macias | 24/134 R |
| 5,657,000 A | 8/1997 | Ellingboe | |
| 5,860,197 A | 1/1999 | Fox | |
| 5,868,696 A | 2/1999 | Giesler et al. | |
| 5,931,112 A * | 8/1999 | Lacan | 114/218 |
| 5,941,696 A | 8/1999 | Fenstermacher et al. | |
| 6,117,115 A | 9/2000 | Hill et al. | |
| 6,123,524 A | 9/2000 | Danby et al. | |
| 6,195,887 B1 | 3/2001 | Danby et al. | |
| 6,213,738 B1 | 4/2001 | Danby et al. | |
| 6,368,080 B1 | 4/2002 | Sipin | |
| 6,494,693 B1 | 12/2002 | Sundén | |
| 2002/0064470 A1 | 5/2002 | Andersen et al. | |
| 2002/0165503 A1 | 11/2002 | Morris et al. | |
| 2003/0021710 A1 | 1/2003 | Miyazawa | |

* cited by examiner

UNIVERSAL TUBE CLAMP ASSEMBLY

TECHNICAL FIELD

The present invention relates to a tube clamp assembly for flexible tubing and, more particularly, to a tube clamp assembly for holding different sizes of flexible tubing to be used in a peristaltic pump.

BACKGROUND OF THE INVENTION

Peristaltic pumps have been widely used for medical and research applications where constant or pulsatile metering of fluids at a relatively low flow rates is desired. Peristaltic pumps are volumetric pumps which progressively compress a flexible tube to propel a fluid along the tube under the influence of rotating members which contact the tube at spaced-apart locations. More specifically, the conventional peristaltic pump provides a circular array of rollers which are driven in a planetary motion against one or more flexible tubes to effect the compression thereof and the resultant pumping of the fluid. Such pumps are commonly used in cardiovascular surgery for circulating blood between a patient and a heart-lung machine. Other common uses for such pumps are the transfer of blood between a patient and a kidney dialyser and the intravenous infusion of medications.

In pumps which utilize peristaltic tubes, or an array of peristaltic tubes, special care must be taken to assure that the tubes deliver fluid at the desired rate. The rate of delivery is a function not only of the rate at which the rollers move along the tube, but also of the inside and outside diameters of the tube, the compression characteristics, the force with which the roller compresses the tube and the tension of the tube within the pump. All these variables must be carefully and precisely controlled to assure consistent and uniform or pulsatile metering rates within and between the delivery tubes.

One of the most easily changed variables in a peristaltic pump is the diameter of the flexible tubing through which the fluid is pumped. Typical tubing varies from an outer diameter of 0.213" to 0.6875", although tubing have greater and lesser diameters is also known. A tubing clamp is utilized in order to accommodate this wide range of tubing sizes in the peristaltic pump, and the clamp is typically configured to receive a clamp insert corresponding to the desired tubing size. Not only does this require a set of clamp inserts to be maintained for all possible tubing sizes, increasing the costs associated with the peristaltic pump, but changing the clamp insert also increases the time and labor required for operating room preparation.

In addition, although clamps do exist that can be adjusted to hold a limited range of tubing sizes without changing an insert, these clamps may often require an additional tool such as a wrench in order to effect the tubing size adjustment and, once again, greatly increase the time and labor required for operating room preparation A strong need therefore exists for a tubing clamp capable of holding a plurality of sizes of flexible tubing without requiring additional set up time or labor intensive manipulation of clamp inserts or adjustments.

SUMMARY OF THE INVENTION

In order to overcome these disadvantages, the present invention provides a clamp assembly for flexible tubing having a housing, at least one movable slide disposed within the housing, an opening defined between the slide and the housing for receiving flexible tubing, and a control element. Rotation of the control element in a first direction displaces the slide in a first predetermined direction, and thereby opens the opening for insertion of flexible tubing. In a preferred embodiment of the invention, each movable slide includes opposing slide elements and each of the slide elements includes a slide recess. Similarly, the housing includes two opposing side supports and each of the side supports includes a support recess. Thus, each opening is defined between the slide recess in the slide and the support recess in the housing.

In a preferred embodiment of the present invention, the control element includes a control knob and an internal surface of the control element includes a cam surface. Each movable slide also includes a cam element which engages a cam surface on the control element. Thus, rotation of the control knob results in movement of the cam surface and the cam element engaged therewith, thereby displacing the movable slide.

A further embodiment of the present invention is directed to a clamp assembly for flexible tubing including a housing, an upper movable slide disposed within the housing, a lower movable slide disposed within the housing that is disposed vertically beneath the upper slide, a plurality of tubing openings defined between the slides and the housing, and a rotatable control element. Rotation of the control element displaces the slides in a predetermined lateral direction. Each of the movable slides includes a slide element which has a slide concavity. Similarly, the housing includes two opposing side supports, each of which includes an upper concavity generally aligned with the slide concavity of the upper movable slide and a lower concavity generally aligned with the slide concavity of the lower movable slide. Accordingly, the plurality of tubing openings are defined between the slide concavities and the upper and lower housing concavities.

The present invention also includes a method of clamping a plurality of flexible tubing including the step of providing a clamp assembly having a housing, at least one movable slide disposed within the housing, openings defined between each side of at least one slide and the housing for receiving flexible tubing, and a control element. The method further includes rotating the control element in a first direction from a neutral position so as to open the opening on first side of the clamp assembly, inserting flexible tubing through the opening, rotating the control element in a second direction, opposite to the first direction, to return to the neutral position, and thereby closing the opening to engage the flexible tubing.

BRIEF DESCRIPTION OF THE DRAWINGS

The above description and other objects, advantages, and features of the present invention will be more fully understood and appreciated by reference to the specification and accompanying drawings, wherein.

DETAILED DISCUSSION OF THE PREFERRED EMBODIMENTS

Figure 1:
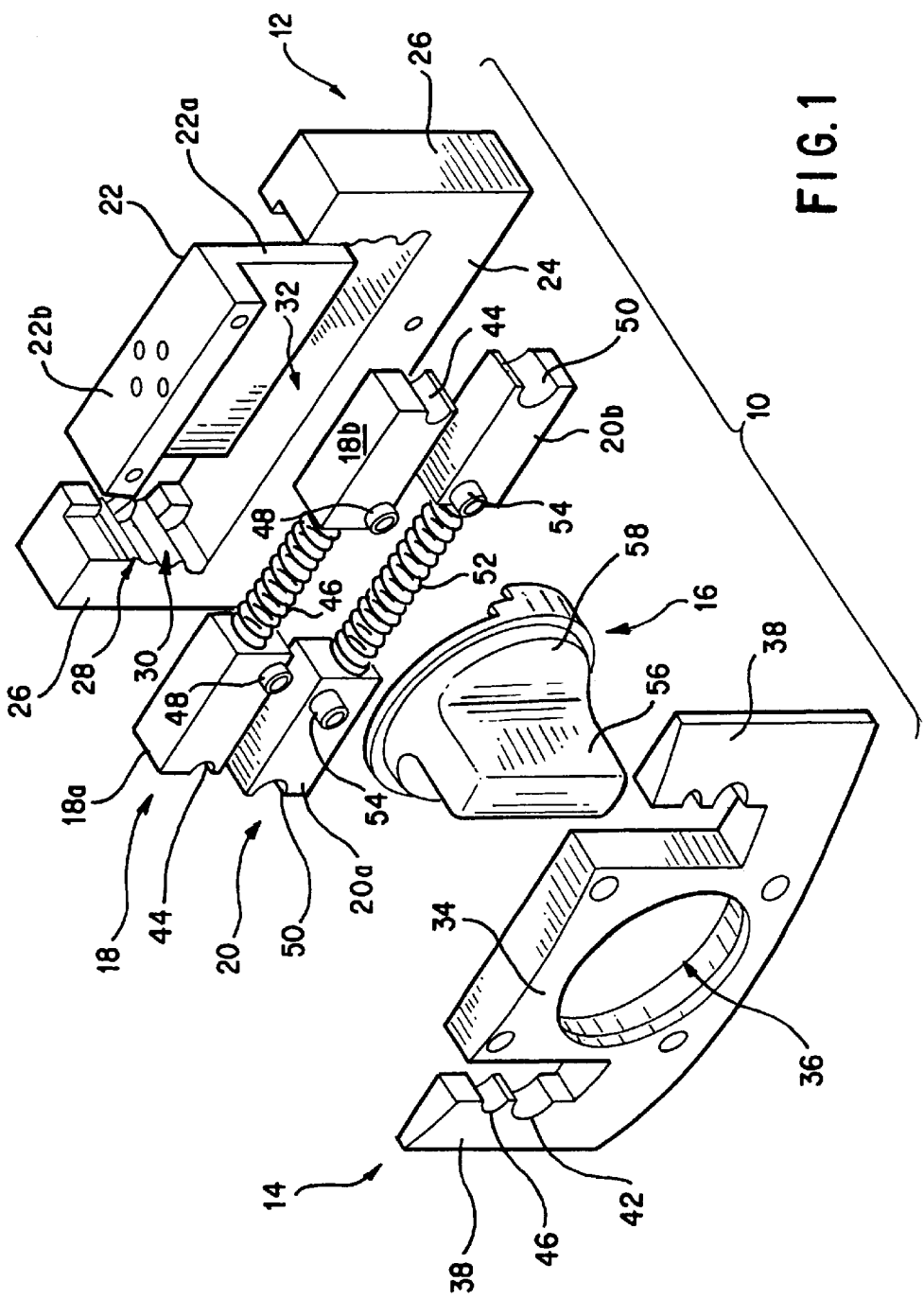
FIG. 1 is an exploded view of the universal tube clamp assembly of the present invention.

Referring to FIG. 1, a preferred embodiment of the universal tube clamp assembly according to the present invention is shown generally by reference numeral 10. The tube clamp assembly 10 includes a base unit 12 and a cover plate 14 secured thereto. Disposed between the base unit 12 and the cover plate 14 are a control knob 16, an upper slide 18, and a lower slide 20. Rotation of the control knob 16 thereby causes retraction of the upper and lower slides on either the right side of the clamp assembly or on the left side of the clamp assembly depending upon the direction of rotation of the control knob 16, as explained in detail below.

The base unit 12 includes an upper support 22 having a rear substantially vertical element 22a and an upper substantially horizontal element 22b. The upper support 22 and a lower support 24 define a base chamber 32 for receiving the upper and lower slides 18, 20. The base unit 12 further includes side supports 26, each of which has a first recess 28 defining a first concavity radius and a second recess 30 defining a second concavity radius. As discussed below in greater detail, the first and second recesses 28 and 30 are configured for receiving flexible tubing having a plurality of outer diameters. In a preferred embodiment, therefore, the radius of the first recess 28 will be greater or lesser than the radius of the second recess 30 so as to accommodate a broader range of tubing diameters.

The cover plate 14 includes a central panel portion 34 having an opening 36 for receiving the rotatable control knob 16. The cover plate 14 further includes opposing side panels 38, each of which includes a first recess 40 and a second recess 42. In the assembled condition, the side panels 38 of the cover plate are aligned with the side supports 26 of the base unit 12. Accordingly, the concavity of the first recess 40 in the cover plate 14 corresponds to the concavity of first recess 28 and second recess 42 of the cover plate 14 corresponds to the concavity of second recess 30.

Upper slide 18 includes a left slide element 18a and a right slide element 18b, with a spring 46 disposed therebetween. Each of the slide elements 18a, 18b include a predefined recess 44 having a radius of concavity which corresponds to first recess 28. Each of the left and right slide elements 18a, 18b further include a cam element 48, the purpose of which is described further below. Similarly, the lower slide 20 includes a left slide element 20a and a right slide element 20b, with a spring 52 disposed therebetween. Each of the lower slide elements 20a, 20b include a recess 50 having a radius of concavity corresponding to the second recess 30 of the side support 26. In addition, each of the lower slide elements 20a, 20b includes a cam element 54, as discussed further below.

Figure 2:
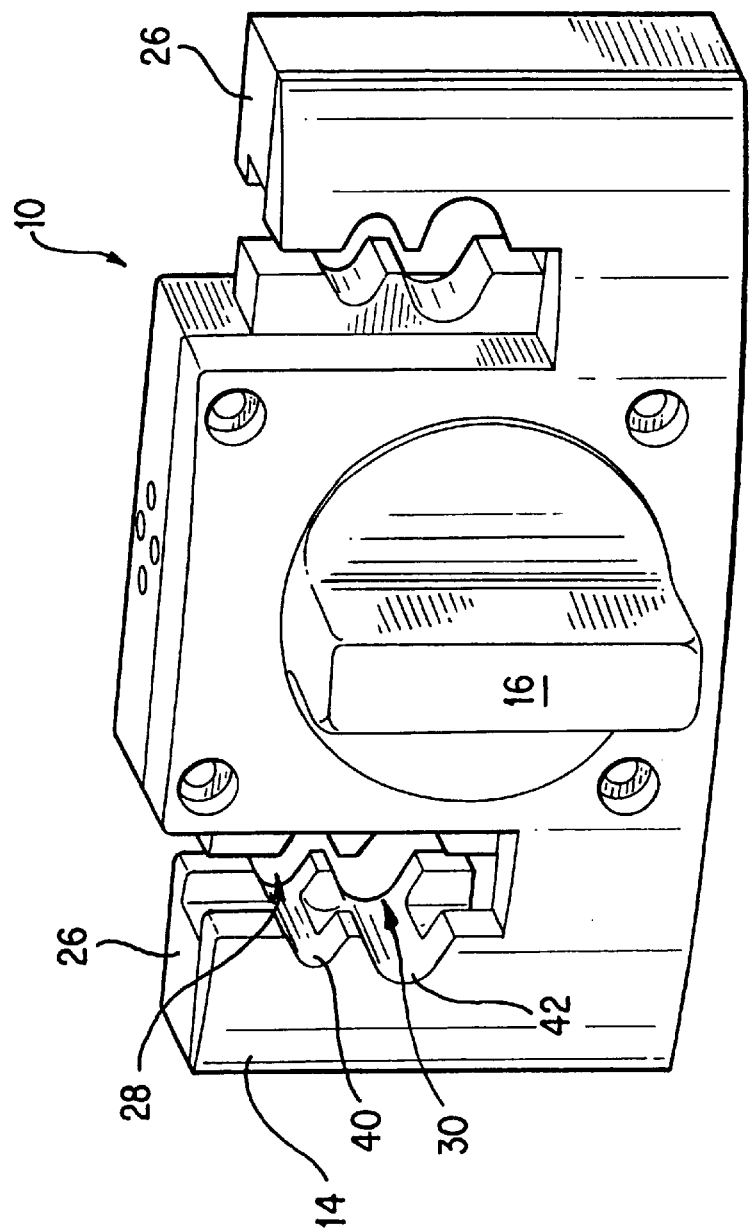
FIG. 2 is a perspective view thereof in an assembled condition.
Figure 6:
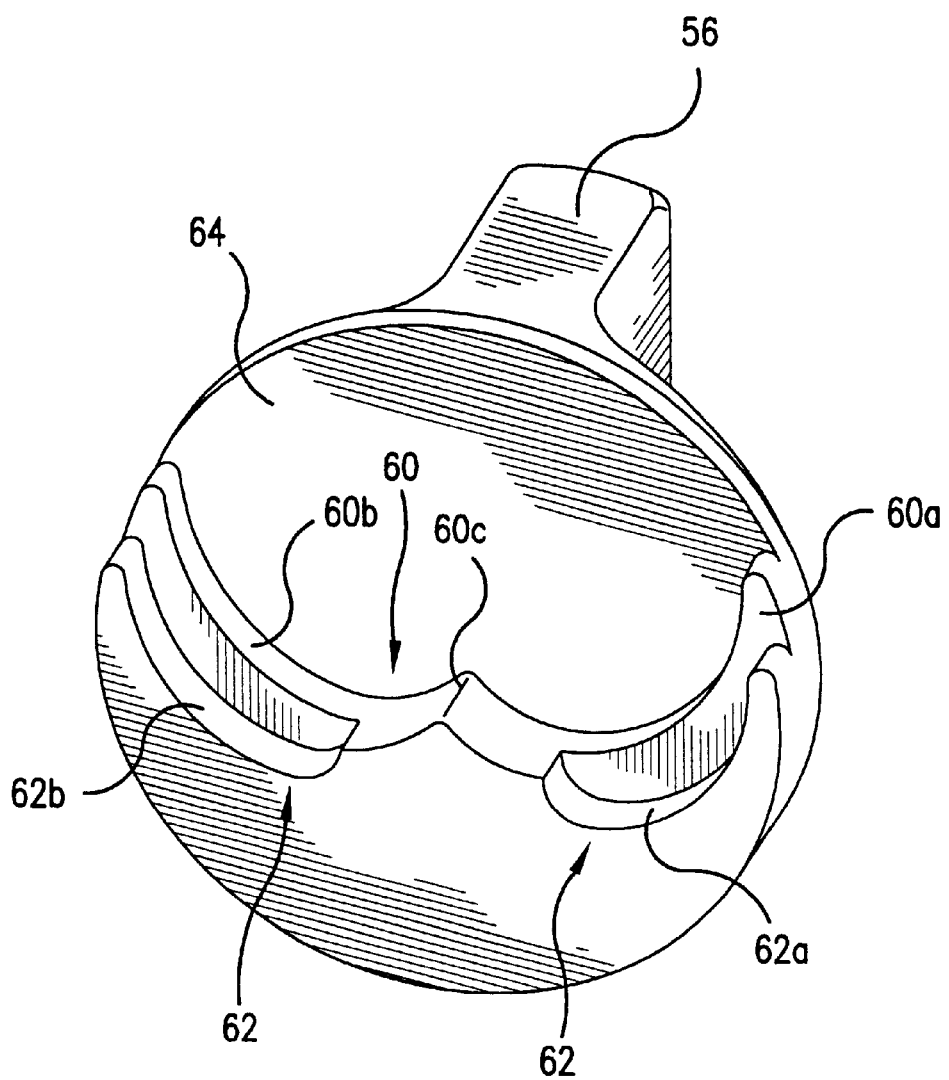
FIG. 6 is a rear perspective view of the control knob.
Figure 7:
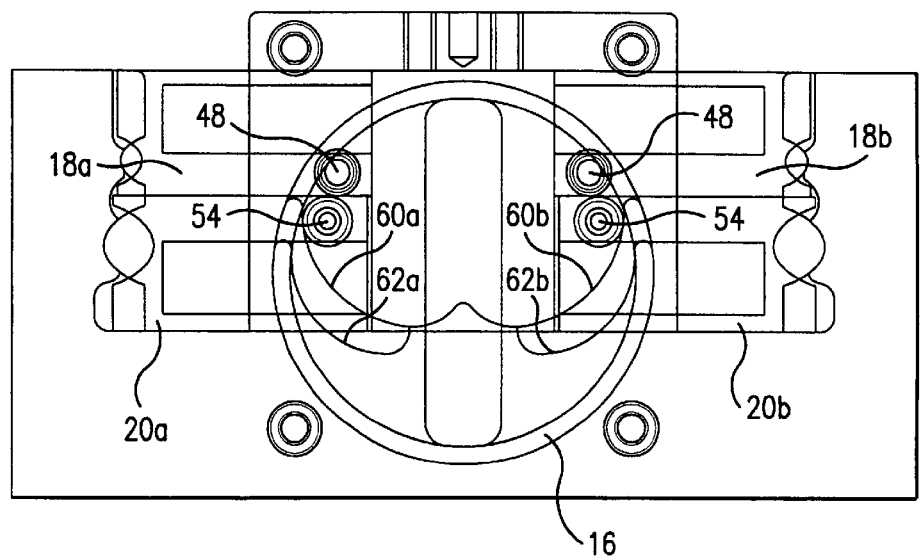
FIG. 7 is a schematic illustration showing the engagement of the cam elements and the cam surfaces when the control knob is in a neutral position.
Figure 8:
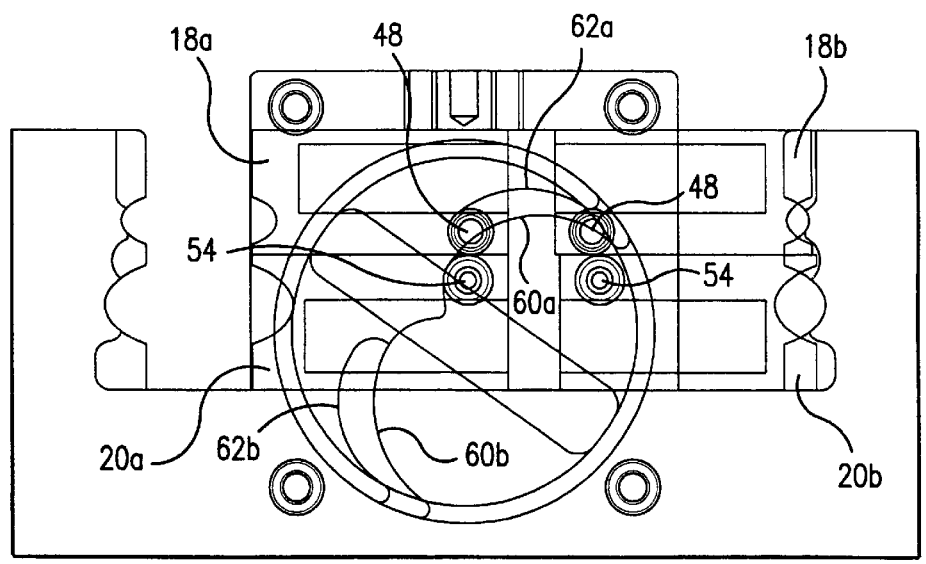
FIG. 8 is a schematic illustration thereof with the control knob rotated in the clockwise direction.
Figure 9:
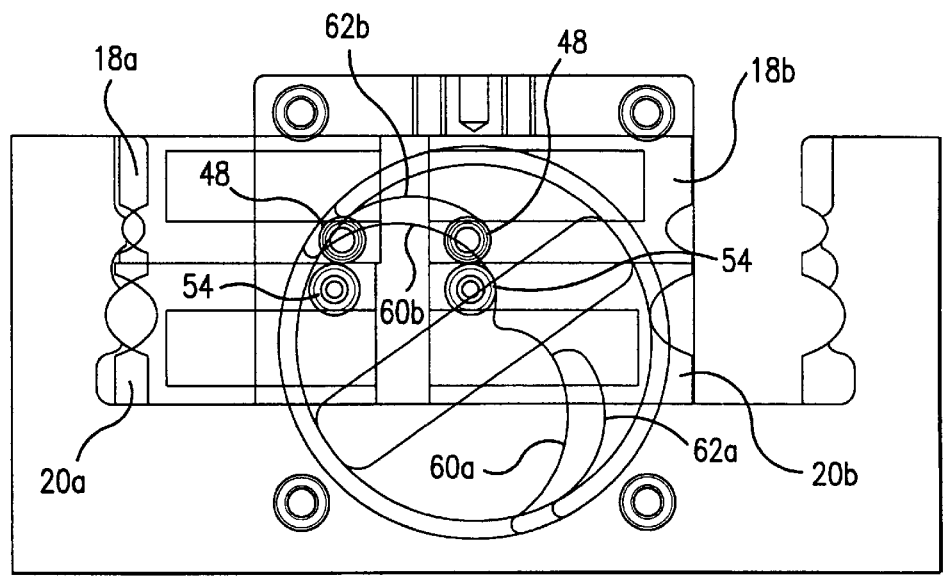
FIG. 9 is a schematic illustration thereof with the control knob rotated in the counterclockwise direction.

The control knob 16 includes a handle portion 56 extending from a front or exterior surface 58 thereof. The handle portion 56 extends through the opening 36 in the cover plate 14 so as to enable a user to easily grasp the handle 56 for rotation. The control knob 16 further includes on a rear or interior surface 64 an upper cam surface 60 and a lower cam surface 62, as shown most clearly in FIG. 6. The upper cam surface 60 includes a left arcuate surface 60a and a right arcuate surface 60b which are joined in the middle by a center surface 60c. The lower cam surface 62 similarly includes a left arcuate surface 62a and a right arcuate surface 62b. When assembled as shown in FIG. 2, cam elements 48 of upper slide 18 are not engaged and cam elements 54 of lower slide 20 are engaged by upper cam surface 60, as shown schematically in FIG. 7. In addition, referring to FIG. 8, when the control knob 16 is rotated in a clockwise direction, cam element 54 associated with slide element 20a moves along upper cam surface 60a and cam element 48 associated with slide element 18a is engaged by lower cam surface 62a. Similarly, as shown in FIG. 9, when the control knob 16 is rotated in a counterclockwise direction, cam element 54 associated with slide element 20b moves along upper cam surface 60b and cam element 48 associated with upper slide element 18b is engaged by lower cam surface 62b.

Figure 3:
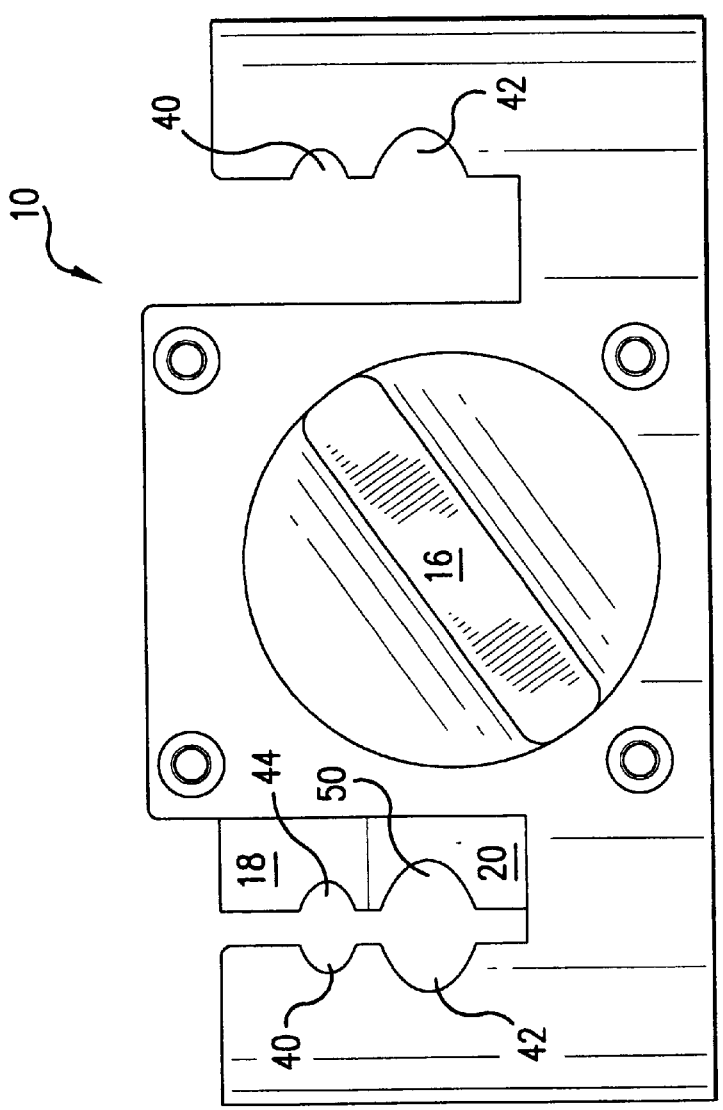
FIG. 3 is a front elevational view thereof illustrating the control knob rotated counter-clockwise and the right side slides retracted for insertion or removal of tubing from the clamp.
Figure 10:
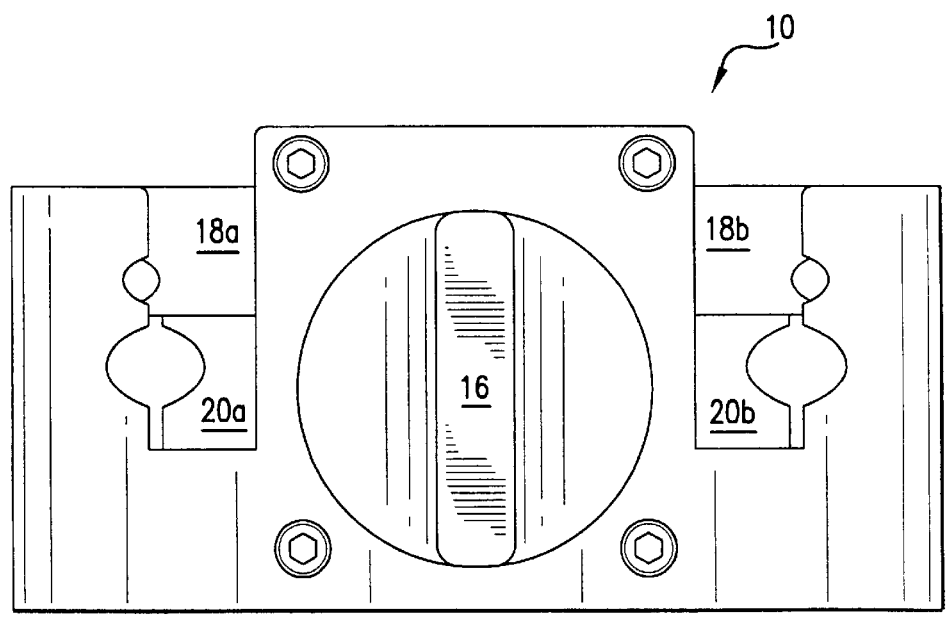
FIG. 10 is a front elevational view of the universal tube clamp assembly illustrating the approximate positions of the slides for holding different sizes of tubing.

Referring to FIG. 2, when the control knob 16 is disposed in a neutral or preferably vertical position, the upper and lower slides are in an extended condition so as to secure flexible tubing within the clamp assembly 10. When the control knob 16 is rotated in the counter-clockwise direction, the upper and lower slides 18, 20 on the right side of the tube clamp assembly 10 are moved to a retracted position, as shown in FIG. 3, thereby allowing flexible tubing to be placed into or removed from the right side of the clamp. In a similar manner, when the control knob 16 is rotated in a clockwise direction, the upper and lower slides 18, 20 on the left side of the clamp assembly 10 are retracted, thus allowing the tubing to be loaded into or removed from the left side of the clamp. As should be apparent to one skilled in the art, the upper and lower slides 18, 20 are designed to move independently of one another. As shown in FIG. 10, the upper slide 18 is in a nominal position for holding a 0.213 inch outer diameter tube while the lower slide 20 is in a nominal position for holding a 0.5625 inch outer tube.

Figure 4:
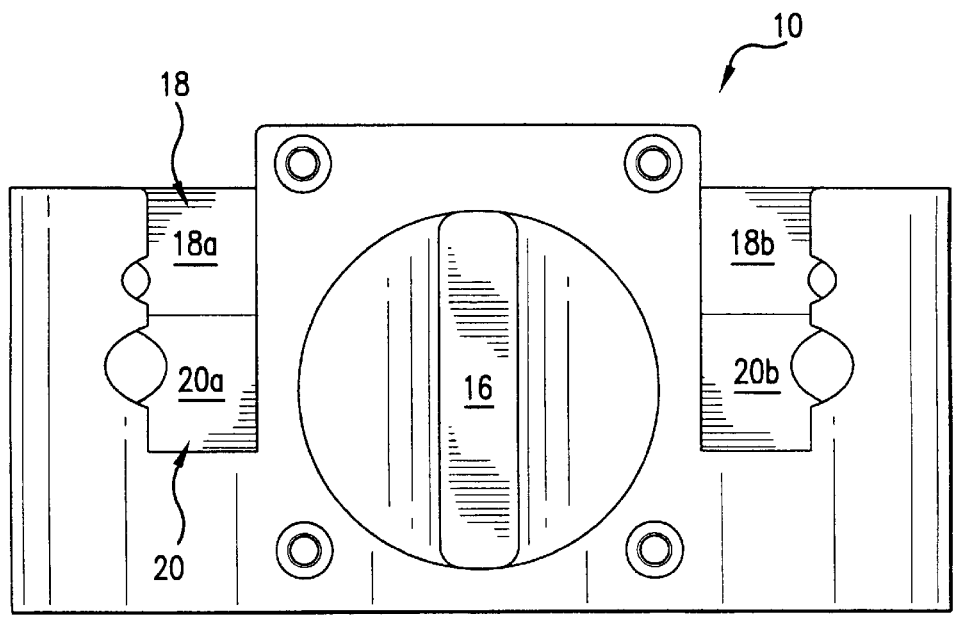
FIG. 4 is front elevational view thereof illustrating the approximate positions of the slides for holding a first size tubing.
Figure 5:
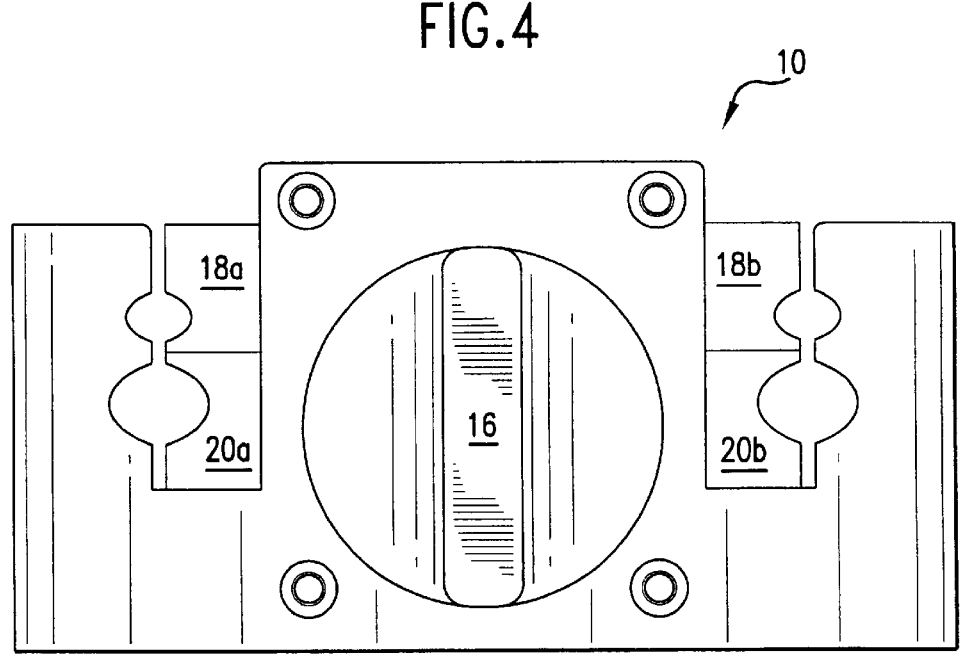
FIG. 5 is a front elevational view thereof illustrating the approximate position of the slides for holding a second diameter tubing.

Referring also to FIG. 4, the clamp assembly 10 is illustrated with the upper and lower slides 18, 20 positioned for holding a 0.213 inch outer diameter tube in the upper slide 18 and a 0.375 inch outer diameter tube in the lower slides 20. Similarly, FIG. 5 illustrates the approximate position of the slides 18, 20 for holding a 0.375 inch outer diameter tube in the upper slide 18 and a 0.5625 inch outer diameter tube in the lower slide 20. As should be clear to one skilled in the art, the universal tube clamp assembly 10 of the present invention can also be designed to hold other ranges of tubing diameters in the slides, for example, a clamp could be designed to hold tubing sizes ranging from 0.213 inch outer diameter to 0.375 inch outer diameter in the upper slide 18 and from 0.375 inch outer diameter to 0.6875 inch outer diameter in the lower slide 20. The particular configuration of the recesses in the slides, base unit 12 and cover plate 14 are designed such that a large range of tubing sizes can be firmly held by the upper and lower slides 18, 20 while minimizing the restriction to the flow of fluid through the tubing. In the preferred embodiment of the present invention, the clamp assembly 10 is capable of holding the typical ranges of individual tube sizes as well as the typical tube sets (i.e., 1:1, 2:1, 4:1) used in peristaltic roller pump.

The spring 46 utilized with the tube clamp assembly 10 of the present invention preferably has a spring rate of about 2.4 lb/in and an uncompressed length of approximately 4.43 in. Similarly, spring 52 preferably has a spring rate of about 2.1 lb/in and an uncompressed length of approximately 5.12 in. The spring rate and uncompressed length of the springs used in the tube clamp assembly can be varied as desired to either increase or decrease the holding force for the tubing and the corresponding effort required to turn the knob to open the clamp. In addition, although the preferred embodiment utilizes springs with a different stiffness because it takes more force to maintain the larger tube in place, it would be within the scope of the present invention to provide a spring 46 and spring 52 having the same stiffness.

Figure 11:
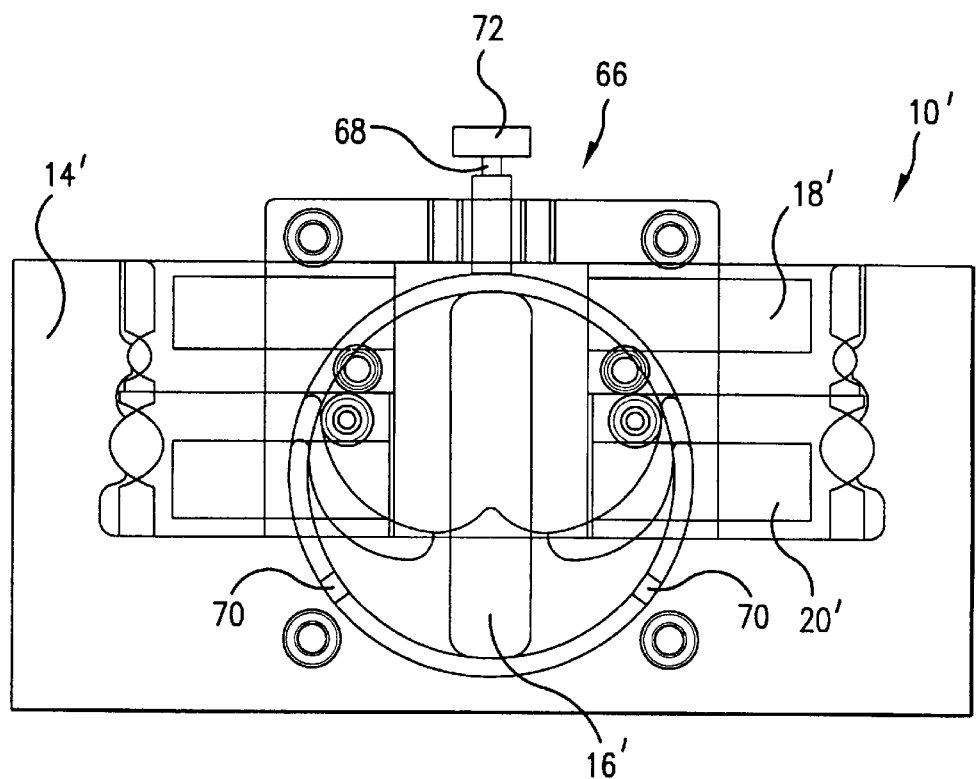
FIG. 11 is a front elevational view of the universal tube clamp assembly according to a further embodiment of the invention.
Figure 12:
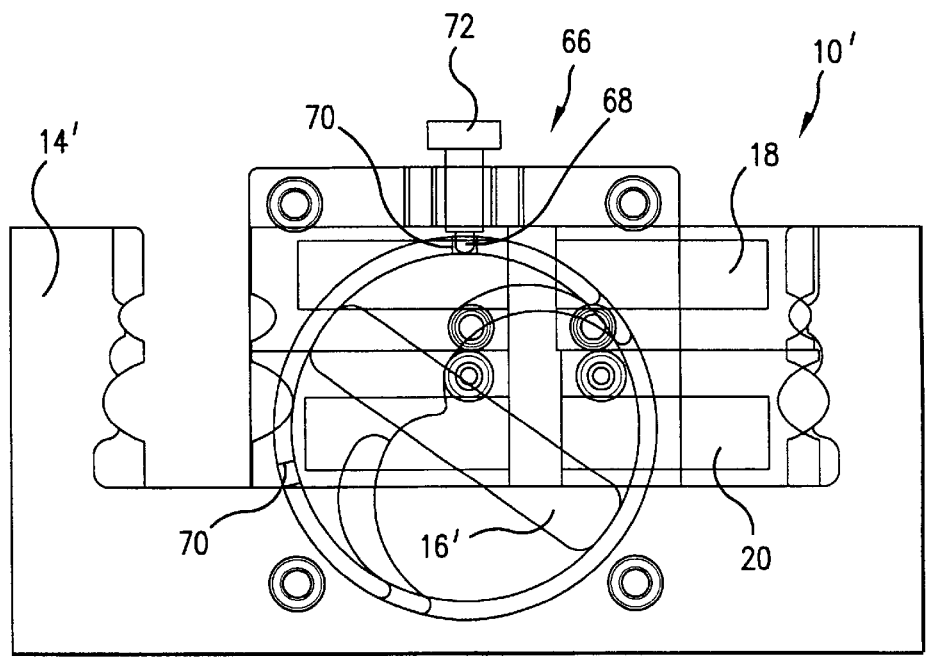
FIG. 12 is a further front elevational view of the tube clamp assembly illustrated in FIG. 11.
Figure 13:
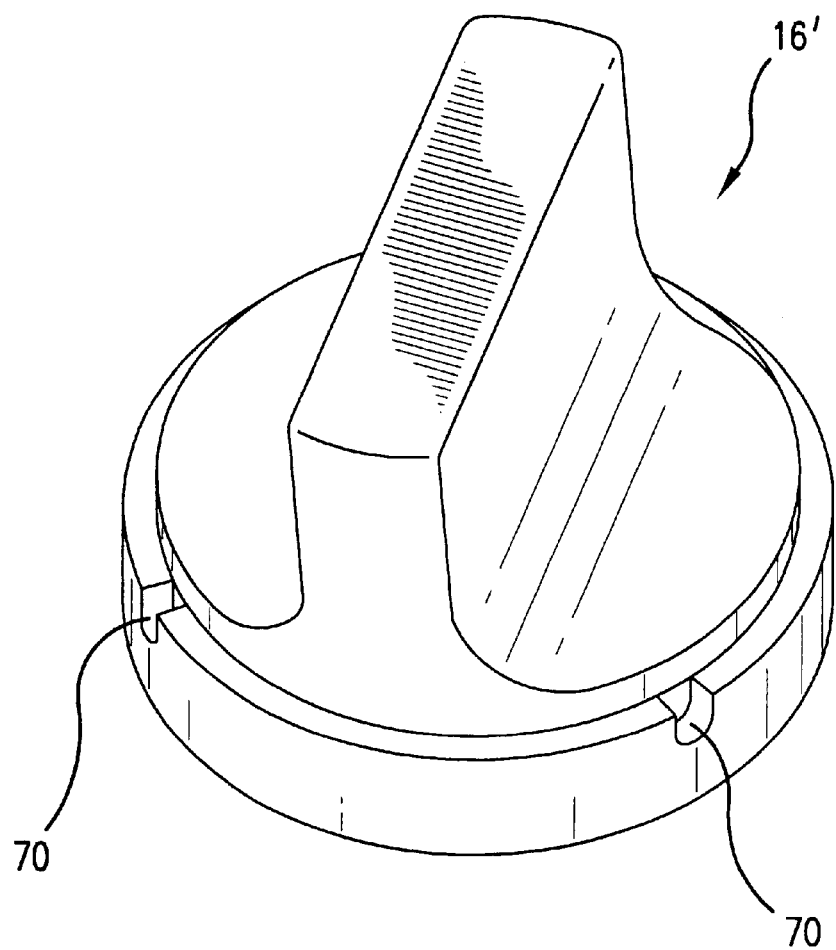
FIG. 13 is a perspective view of the control knob shown in FIG. 11.

According to a further preferred embodiment of the present invention, the tube clamp assembly 10' includes a lock mechanism 66 for holding the control knob 16' and slides 18', 20' open on either side of the clamp while the tubes are being inserted into or removed from the clamp, as shown in FIGS. 11–13. The lock mechanism 66 preferably includes a spring loaded pin 68, such as a retractable spring loaded plunger, mounted in the cover plate 14'. Referring to FIG. 13, the control knob 16' includes two recesses 70 in the front surface thereof. When the control knob 16' is turned fully open in either the clockwise or counterclockwise direction, the spring loaded pin 68 is engaged within one of the knob recesses 70, thereby locking the control knob 16' in position. In order to unlock the control knob 16', the top 72 of the pin 68 is pulled in an upward direction. End forces on the pin may vary as the pin is retracted on the order of 0.12 lbs to 3.0 lbs. In a further embodiment of the invention, the pin 68 may also be locked in an open position. If the pin 68 is locked in an open position, then the control knob will not be locked when fully opened, and if the pin 68 is not locked open then the control knob will be locked when fully open; thus providing even further versatility for the end user.

While the present invention has been described with respect to the preferred embodiments, it is to be understood that variations and modifications may be resorted as will be apparent to those skilled in the art. Such variations and modifications are to be considered within the purview and the scope of the claims appended hereto.

What is claimed is:

1. A clamp assembly for flexible tubing comprising:
    a housing;
    at least one movable slide disposed within said housing;
    an opening defined between each side of said at least one slide and said housing for receiving flexible tubing; and
    a control element, rotational movement of said control element displacing said at least one slide in a predetermined lateral direction.

2. The clamp assembly of claim 1 wherein said at least one movable slide includes opposing side slide elements, each of said side slide elements including a slide recess.

3. The clamp assembly of claim 2 wherein said housing includes an upper support, a lower support, and two opposing side supports, said side supports including a support recess.

4. The clamp assembly of claim 3 wherein each said opening is defined between said slide recess and said support recess.

5. The clamp assembly of claim 1 wherein said control element includes a control knob, an internal surface of said control element including a cam surface.

6. The clamp assembly of claim 5 wherein said at least one movable slide includes at least one cam element, said at least one cam element engaging said cam surface on said control element.

7. The clamp assembly of claim 6 wherein said at least one movable slide includes opposing side slide elements, each of said side slide elements including one said cam element, and wherein said cam surface includes two arcuate cam surfaces, each said cam element engaging a respective said arcuate cam surface.

8. The clamp assembly of claim 1 wherein said at least one movable slide includes opposing side slide elements and a spring disposed therebetween.

9. The clamp assembly of claim 1 further comprising a lock mechanism for holding said at least one slide in a displaced position.

10. A clamp assembly for flexible tubing comprising:
    a housing;
    an upper movable slide disposed within said housing;
    a lower movable slide disposed within said housing, said lower slide being disposed vertically beneath said upper slide;
    a plurality of tubing openings defined between said slides and said housing;
    a rotatable control element, rotation of said control element displacing said slides in a predetermined lateral direction.

11. The clamp assembly of claim 10 wherein each of said movable slides includes opposing side slide elements, each of said side slide elements including a slide concavity.

12. The clamp assembly of claim 11 wherein said housing includes two opposing side supports, each said side support including an upper concavity generally aligned with said upper movable slide and a lower concavity generally aligned with said lower movable slide.

13. The clamp assembly of claim 12 wherein said plurality of tubing openings are defined between said slide concavities and said upper and lower concavities.

14. The clamp assembly of claim 10 wherein said control element includes an upper cam surface and a lower cam surface.

15. The clamp assembly of claim 14 wherein each of said upper and lower cam surfaces includes two arcuate cam surfaces.

16. The clamp assembly of claim 14 wherein each said movable slide includes two cam elements, each said cam element engaging a respective said cam surface on said control element.

17. The claim assembly of claim 10 further comprising a lock mechanism holding said slides in a displaced position.

18. A method of clamping a plurality of flexible tubings comprising the steps of:
    providing a clamp assembly having a housing, at least one movable slide disposed within said housing, openings defined between each side of said at least one slide and said housing for receiving flexible tubing, and a control element;
    rotating the control element in a first direction from a neutral position so as to open the opening on a first side of the clamp assembly;
    inserting a flexible tubing through the opening;

rotating the control element in a second direction, opposite to the first direction, to return to the neutral position, thereby closing the opening to engage the flexible tubing.

19. The method of claim 18 further comprising:

after returning the control element to the neutral position, rotating the control element further in the second direction from the neutral position so as to open the opening on the second side of the clamp assembly;

inserting a second flexible tubing through the opening;

rotating the control element in the first direction to return to the neutral position, thereby closing the opening to engage the second flexible tubing.

20. The method of claim 18 further comprising:

after rotating the control element in the first direction, locking the control element in an open position; and before rotating the control element in the second direction, unlocking the control element.

* * * * *